United States Patent
Fey

(10) Patent No.: US 9,696,289 B2
(45) Date of Patent: Jul. 4, 2017

(54) METHOD AND CONTROL UNIT FOR COMPENSATING FOR A VOLTAGE OFFSET OF A TWO-POINT LAMBDA SENSOR

(71) Applicant: Robert Bosch GmbH, Stuttgart (DE)

(72) Inventor: Michael Fey, Wiernsheim (DE)

(73) Assignee: Robert Bosch GmbH, Stuttgart (DE)

(*) Notice: Subject to any disclaimer, the term of this patent is extended or adjusted under 35 U.S.C. 154(b) by 273 days.

(21) Appl. No.: 14/401,483

(22) PCT Filed: Apr. 17, 2013

(86) PCT No.: PCT/EP2013/057954
§ 371 (c)(1),
(2) Date: Nov. 14, 2014

(87) PCT Pub. No.: WO2013/171015
PCT Pub. Date: Nov. 21, 2013

(65) Prior Publication Data
US 2015/0135802 A1   May 21, 2015

(30) Foreign Application Priority Data
May 15, 2012 (DE) .......... 10 2012 208 092

(51) Int. Cl.
*F02D 41/00* (2006.01)
*G01N 33/00* (2006.01)
(Continued)

(52) U.S. Cl.
CPC ..... *G01N 33/0073* (2013.01); *F02D 41/1454* (2013.01); *F02D 41/2474* (2013.01); *G01M 15/104* (2013.01); *G01N 33/0006* (2013.01); *G01R 19/165* (2013.01); *F02D 41/123* (2013.01); *F02D 41/2454* (2013.01)

(58) Field of Classification Search
CPC ............. F02D 41/1454; F02D 41/2474; F02D 41/2454; F02D 41/123; G01R 19/165;
(Continued)

(56) References Cited

U.S. PATENT DOCUMENTS 4,502,444 A    3/1985 Rubbo et al.
9,291,112 B2 *  3/2016 Fey .................. F02D 41/00
(Continued)

FOREIGN PATENT DOCUMENTS

CN    101685078 A    3/2010
CN    102102567 A    6/2011
(Continued)

OTHER PUBLICATIONS

International Search Report for PCT/EP2013/057954, issued on Aug. 1, 2013.

*Primary Examiner* — Blake A Tankersley
(74) *Attorney, Agent, or Firm* — Norton Rose Fulbright US LLP; Gerard Messina

(57) ABSTRACT

A method is described for compensating for a voltage offset in a voltage-lambda characteristic curve of a two-point lambda sensor in relation to a reference voltage-lambda characteristic curve of the two-point lambda sensor, the two-point lambda sensor being situated in an exhaust duct of an internal combustion engine. It is provided that the slope of the voltage-lambda characteristic curve is determined for an output voltage of the two-point lambda sensor and is compared to the slope of a reference voltage-lambda characteristic curve at equal output voltage, and the voltage offset is determined from a deviation of the determined slope of the voltage-lambda characteristic curve from the slope of the reference voltage-lambda characteristic curve. Also described is a control unit for carrying out the method. The method and the control unit enable the determination of and compensation for a voltage offset of a two-point lambda sensor caused by aging or manufacturing tolerances.

13 Claims, 2 Drawing Sheets

(51) Int. Cl.
*F02D 41/14* (2006.01)
*G01M 15/10* (2006.01)
*G01R 19/165* (2006.01)
*F02D 41/12* (2006.01)
*F02D 41/24* (2006.01)

(58) Field of Classification Search
CPC ........... G01N 33/0006; G01N 33/0073; G01N 27/4175; G01M 15/104
See application file for complete search history.

(56) References Cited

U.S. PATENT DOCUMENTS

| | | | | |
|---|---|---|---|---|
| 9,354,213 B2* | 5/2016 | Fey | ................. | G01N 33/0006 |
| 2008/0087260 A1* | 4/2008 | Yamada | .............. | F02D 41/0085 |
| | | | | 123/703 |

FOREIGN PATENT DOCUMENTS

| | | |
|---|---|---|
| CN | 102108906 A | 6/2011 |
| DE | 102007016276 | 10/2008 |
| DE | 102010027984 | 10/2011 |
| DE | 102010041809 | 4/2012 |
| EP | 0134672 | 3/1985 |
| EP | 1143132 | 10/2001 |
| JP | S6050934 A | 3/1985 |
| JP | H07-127505 A | 5/1995 |
| JP | H07-224705 A | 8/1995 |
| JP | H09-291843 A | 11/1997 |
| JP | 2004-183-585 A | 7/2004 |
| JP | 2008-095627 A | 4/2008 |
| WO | 2008/122369 A2 | 10/2008 |

* cited by examiner

METHOD AND CONTROL UNIT FOR COMPENSATING FOR A VOLTAGE OFFSET OF A TWO-POINT LAMBDA SENSOR

FIELD OF THE INVENTION

The present invention relates to a method for compensating for a voltage offset in a voltage-lambda characteristic curve in relation to a reference voltage-lambda characteristic curve of the two-point lambda sensor, the two-point lambda sensor being situated in the exhaust gas of an internal combustion engine.

The present invention furthermore relates to a control unit for carrying out the method.

BACKGROUND INFORMATION

In modern internal combustion engines, lambda sensors for determining the composition of the exhaust gas and for controlling the internal combustion engine are used to optimize the pollutant emission and the exhaust gas aftertreatment. Lambda sensors determine the oxygen content of the exhaust gas, which is used to regulate the air-fuel mixture supplied to the internal combustion engine and therefore the exhaust gas lambda upstream from a catalytic converter. The air and fuel supply of the internal combustion engine are regulated via a lambda control loop in such a way that an optimum composition of the exhaust gas is achieved for the exhaust gas aftertreatment by the catalytic converters provided in the exhaust duct of the internal combustion engine. In gasoline engines, lambda is generally regulated to 1, i.e., a stoichiometric ratio of air to fuel. The pollutant emission of the internal combustion engine may thus be minimized.

Various forms of lambda sensors are used. In a two-point lambda sensor, which is also referred to as a jump sensor or Nernst sensor, the voltage-lambda characteristic curve has a sudden drop at lambda=1. It therefore essentially permits the differentiation between rich exhaust gas ($\lambda<1$) during operation of the internal combustion engine with excess fuel and lean exhaust gas ($\lambda>1$) during operation with excess air and enables a regulation of the exhaust gas to a lambda of 1.

A broadband lambda sensor, also referred to as a continuous or linear lambda sensor, enables the measurement of the lambda value in the exhaust gas in a broad range around lambda=1. Therefore, for example, an internal combustion engine may also be regulated to a lean operation with excess air.

A continuous lambda regulation upstream from the catalytic converter is also possible by way of a linearization of the sensor characteristic curve using a more cost-effective two-point lambda sensor in a restricted lambda range. The requirement for this purpose is that an unambiguous relationship exists between the sensor voltage of the two-point lambda sensor and lambda. This relationship must exist over the entire service life of the two-point lambda sensor, since otherwise the precision of the regulation is inadequate and impermissibly high emissions may occur. This condition is not met due to manufacturing tolerances and aging effects of the two-point lambda sensor.

To carry out a continuous lambda regulation using a two-point lambda sensor, determining and compensating for a voltage offset of the existing voltage-lambda characteristic curve in relation to a reference voltage-lambda characteristic curve of the two-point lambda sensor, which is constant over the entire lambda range, by an adjustment of the sensor voltage during overrun fuel cutoff of the internal combustion engine, in which no fuel is supplied to the internal combustion engine, is known. Building thereon, the publication DE 10 2010 027 984 A1 describes a method for operating an exhaust system of an internal combustion engine, in which at least one parameter of the exhaust gas flowing in an exhaust duct is detected by an exhaust sensor. It is provided that during an operating state of the internal combustion engine in which injection and combustion of fuel do not occur, fresh air is supplied to the exhaust duct upstream from the exhaust sensor with the aid of a fresh air supply associated with the exhaust system, and the exhaust sensor is adjusted during this and/or thereafter.

Sufficiently good compensation of the voltage offset is only possible, however, if it is equally strongly pronounced not only in the event of overrun fuel cutoff with correspondingly oxygenated exhaust gas, but rather in the entire lambda range. This may be the case if the voltage offset has a single cause. However, there are typically multiple superimposed causes for a deviation of the voltage-lambda characteristic curve in relation to the reference voltage-lambda characteristic curve. These may be pronounced at different strengths in various lambda ranges, whereby the voltage offset changes as a function of the exhaust gas lambda. In particular, the causes may be pronounced at different strengths in the lean lambda range and in the rich lambda range. Such a voltage offset dependent on the lambda cannot be sufficiently compensated for by an adjustment in the event of overrun fuel cutoff. A further disadvantage of the method is that modern engine concepts have fewer and fewer overrun phases, which restricts the possibility of such an overrun adjustment.

Therefore, two-point lambda sensors are usually used upstream from the catalytic converter with a two-point regulation. This has the disadvantage that in operating modes for which a lean or rich air-fuel mixture is necessary, for example, for catalytic converter diagnosis or for component protection, the target lambda may only be set by pilot control, but may not be regulated.

SUMMARY

It is the object of the present invention to provide a simple and reliable method for compensating for a voltage offset of a two-point lambda sensor during operation of the two-point lambda sensor, to enable continuous lambda regulation using the two-point lambda sensor.

It is furthermore the object of the present invention to provide a corresponding control unit for carrying out the method.

The object of the present invention relating to the method is achieved in that for an output voltage of the two-point lambda sensor, the slope or a measure of the slope of the voltage-lambda characteristic curve is determined and is compared to the slope or the measure of the slope of the reference voltage-lambda characteristic curve at the same output voltage, and the voltage offset is determined from a deviation of the determined slope or the measure of the slope of the voltage-lambda characteristic curve from the slope or the measure of the slope of the reference voltage-lambda characteristic curve. The reference voltage-lambda characteristic curve corresponds to the voltage-lambda characteristic curve of an unaged two-point lambda sensor. It defines the setpoint curve of the two-point lambda sensor within the scope of the manufacturing tolerances, for which the lambda regulation of the internal combustion engine is designed. There is an unambiguous relationship between the output voltage of the two-point lambda sensor and the slope ($\Delta U/$ $\Delta\lambda)_{Ref}$ of the reference voltage-lambda characteristic curve for the reference voltage-lambda characteristic curve. If a voltage offset of the voltage-lambda characteristic curve in relation to the reference voltage-lambda characteristic curve exists in the case of the two-point lambda sensor used, this association between measured slope $(\Delta U/\Delta\lambda)_{mess}$ and the output voltage no longer applies. A deviation of the slope of the voltage-lambda characteristic curve of the present two-point lambda sensor from the slope of the reference voltage-lambda characteristic curve at a predefined output voltage may be unambiguously associated with a voltage offset.

The method enables the determination of the voltage offset within the regulating range of the two-point lambda sensor in a lambda range around 1, as predominantly exists during regular operation of the internal combustion engine. The determination of the voltage offset is therefore not linked to operating parameters of the internal combustion engine which result in a particular exhaust gas composition, for example, the overrun phases, which occur very rarely in modern engine concepts. Cost-effective two-point lambda sensors may be used for continuous lambda regulation by the determination and compensation of a voltage offset induced by manufacturing tolerances and aging.

A simple determination of the slope of the voltage-lambda characteristic curve and therefore a voltage offset may be achieved in that, starting from an output voltage of the two-point lambda sensor, a measured voltage change $\Delta U_{mess}$ of the two-point lambda sensor after a predefinable lambda change $\Delta\lambda$ is compared to a reference voltage change $\Delta U_{Ref}$ of the reference voltage-lambda characteristic curve in the case of an equal lambda change $\Delta\lambda$, and the voltage offset is determined from a deviation of measured voltage change $\Delta U_{mess}$ from reference voltage change $\Delta U_{Ref}$. $\Delta U_{meas}/\alpha\lambda$ represents the slope of the voltage-lambda characteristic curve, and $\Delta U_{Ref}/\Delta\lambda$ represents the slope of the reference voltage-lambda characteristic curve. In the event of equal predefined lambda change $\Delta\lambda$ voltage change $\Delta U$ is a measure of the slope and therefore may be used directly for the determination of the voltage offset. The lambda range in which the voltage offset is to be determined may be established by the selection of the output voltage of the two-point lambda sensor at which the slope of the voltage-lambda characteristic curve is determined Lambda change $\Delta\lambda$ may be achieved by a targeted change of the air-fuel mixture supplied to the internal combustion engine. Since the output voltage of the two-point lambda sensor upstream from the catalytic converter must react very rapidly to lambda changes, the lambda changes must only be applied briefly. The method therefore allows a very rapid determination of the voltage offset.

According to a preferred embodiment variant of the present invention, it may be provided that the voltage offset is determined for the entire lambda range of the two-point lambda sensor, or values of the voltage offset are determined for various lambda ranges, in particular for a rich lambda range and a lean lambda range. Depending on its cause, the voltage offset may be of different sizes for various lambda ranges. Due to the possibility of determining the voltage offset separately for various lambda ranges, the voltage offset may be compensated for in an adapted way as a function of the lambda range. Many causes of a voltage offset have effects of different strengths in the lean lambda range and in the rich lambda range. This may be adapted to by separate measurement and compensation of the voltage offset in the case of lean exhaust gas mixtures and in the case of rich exhaust gas mixtures.

According to a further method variant, it may be provided that predefinable lambda change $\Delta\lambda$ is set intentionally and/or the determination of the voltage offset is carried out in the case of a system-related lambda change $\Delta\lambda$. Voltage change $\Delta U$ in the case of a predefined output voltage of the two-point lambda sensor may be determined by an active, intentionally predefined lambda change $\Delta\lambda$. System-related active lambda changes, for example, as may occur for catalytic converter diagnoses, sensor dynamic diagnoses, or phases using two-point lambda regulation, may be used if necessary to obtain additional measurements for voltage changes, without having to carry out an extra active lambda change for this purpose.

The compensation of a voltage offset may be improved in that measured voltage change $\Delta U_{mess}$ is determined, repeatedly proceeding from an output voltage of the two-point lambda sensor, and/or measured voltage change $\Delta U_{mess}$ is determined in the case of positive and negative predefinable lambda changes $\Delta\lambda$, and the determination of the voltage offset is carried out from averaged or filtered measured voltage changes $\Delta U_{mess}$. The repetition of the determination of voltage change $\Delta U_{mess}$ enables a plausibility check of the offset compensation. On the one hand, the recognition precision of a voltage offset may be increased; on the other hand, the setpoint lambda is maintained in the chronological average by the measurement of voltage change $\Delta U_{mess}$ by multiple immediately successive lambda changes $\Delta\lambda$ having opposing directions and subsequent averaging or filtering of the measured values.

A further improvement in the determination of a voltage offset may be achieved in that measured voltage changes $\Delta U_{mess}$ are determined, proceeding from various output voltages of the two-point lambda sensor and the voltage offsets determined therefrom are checked for plausibility by comparison.

The absolute value and/or the type and/or the duration of predefinable lambda change $\Delta\lambda$ may be selected as a function of exhaust gas conditions or operating conditions of the internal combustion engine. Lambda change $\Delta\lambda$ may be carried out, for example, by a jump, a ramp, by wobbling, by positive or negative lambda changes $\Delta\lambda$, or by arbitrary combinations thereof. The absolute value and/or the type and/or the duration of predefinable lambda change $\Delta\lambda$ may be predefined as a function of the exhaust gas conditions or the operating conditions of the internal combustion engine in such a way that an unambiguous and reliable analysis of the determined slope or determined voltage change $\Delta U_{mess}$ may be carried out.

In systems which permit an overrun adjustment, it may be provided that the determined voltage offset is checked for plausibility by an adjustment of the measured output voltage of the two-point lambda sensor to the reference voltage-lambda characteristic curve in the event of an overrun fuel cutoff of the internal combustion engine. This is advantageous in particular if active lambda change $\Delta\lambda$ is itself subject to tolerances.

In the event of a recognized voltage offset of the two-point lambda sensor, it may be provided that the determined voltage offset of the voltage-lambda characteristic curve is completely or partially compensated for and/or the voltage offset is compensated for as a function of the lambda range of the voltage-lambda characteristic curve. It is frequently not necessary to compensate completely for a voltage offset of the voltage-lambda characteristic curve. It may be sufficient if the voltage offset is only compensated enough that the corrected voltage-lambda characteristic curve corresponds sufficiently well to the reference voltage-lambda characteristic curve. In such cases, it may be sufficient to only determine the voltage offset at a few points of the voltage-lambda characteristic curve, even if the actual characteristic curve shift is caused by multiple superimposed effects.

According to a particularly preferred embodiment variant of the present invention, it may be provided that causes of the voltage offset are determined from the curve of the voltage offset as a function of lambda, and/or measures for avoiding or reducing the causes of the voltage offset are taken. Thus, for example, it may occur that the voltage-lambda characteristic curve of the two-point lambda sensor is increasingly shifted in the rich lambda range by a fixed absolute value toward lower output voltages, since the sensor is operated excessively hot. In this case, the heating power of the sensor heater may be reduced and the voltage offset may thus at least be reduced.

The determination of the voltage offset at a predefined output voltage and therefore in a predefined lambda range may be achieved in that a predefined output voltage of the two-point lambda sensor is actively set to determine the voltage offset, or the determination of the voltage offset is carried out when the predefined output voltage is set based on the desired operating conditions of the internal combustion engine. Actively approaching the desired output voltage is reasonable in particular if offset compensation from earlier operating cycles of the internal combustion engine is not yet present. In contrast, if a compensation of the voltage offset has already been carried out in a preceding operating cycle and the data are accordingly present, renewed adjustment may be carried out passively if the desired output voltage is presently provided during the regular operation of the internal combustion engine.

The object of the present invention relating to the control unit is achieved in that the control unit is designed for the purpose of setting a predefinable lambda change $\Delta\lambda$ of the exhaust gas, the control unit has measuring means for determining a voltage change $\Delta U_{mess}$ of the two-point lambda sensor as a reaction to defined lambda change $\Delta\lambda$ to a reference voltage-lambda characteristic curve of the two-point lambda sensor is stored in the control unit, the control unit has a program sequence for comparing measured voltage change $\Delta U_{mess}$ of the two-point lambda sensor after predefinable lambda change $\Delta\lambda$ to a reference voltage change $\Delta U_{Ref}$ of the reference voltage-lambda characteristic curve in the event of an equal lambda change $\Delta\lambda$ and the control unit has a program sequence for determining a voltage offset of the present voltage-lambda characteristic curve of the two-point lambda sensor in relation to the reference voltage-lambda characteristic curve from a deviation of measured voltage change $\Delta U_{mess}$ from reference voltage change $\Delta U_{Ref}$. The control unit enables the determination of a voltage offset of a two-point lambda sensor as a function of the present lambda range. Therefore, the voltage offset may be compensated for, whereby a use of the two-point lambda sensor for a continuous lambda regulation is made possible.

DETAILED DESCRIPTION

Figure 1:
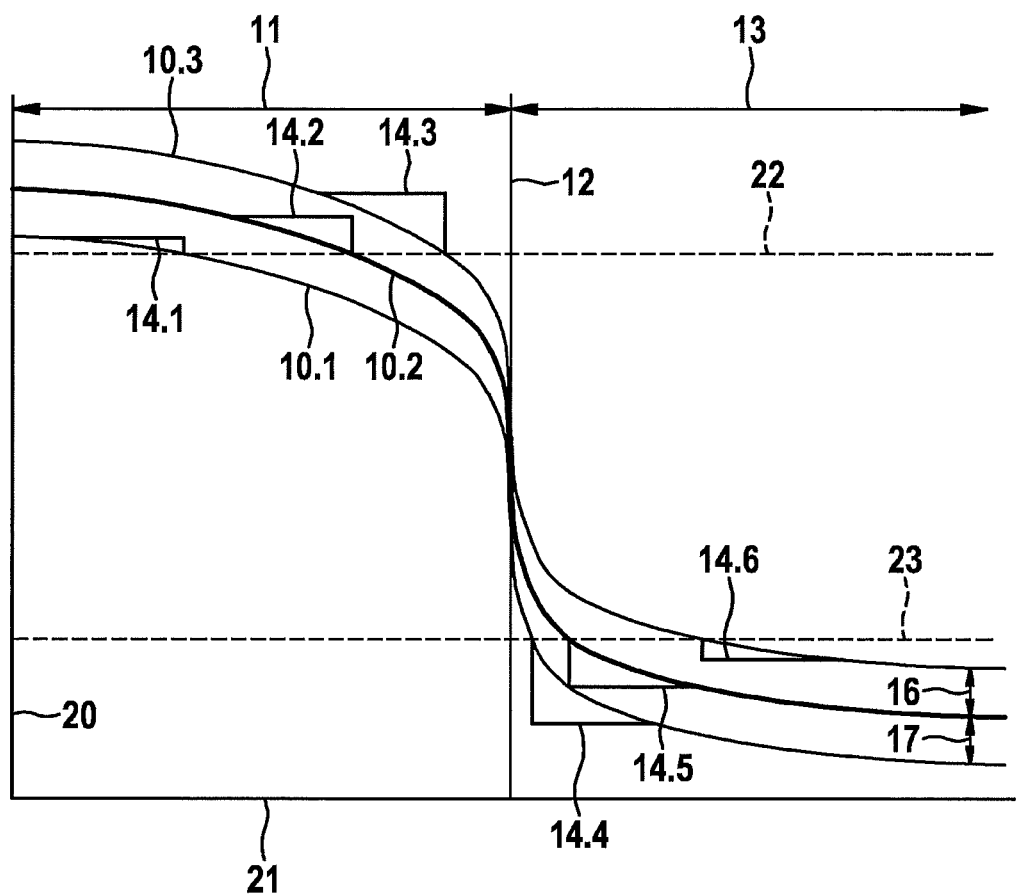
FIG. 1 shows voltage-lambda characteristic curves of a two-point lambda sensor having constant voltage offsets in relation to a reference voltage-lambda characteristic curve.

FIG. 1 shows voltage-lambda characteristic curves 10.1, 10.3 of a two-point lambda sensor having constant voltage offsets 16, 17 in relation to a reference voltage-lambda characteristic curve 10.2. Characteristic curves 10.1, 10.2, 10.3 are plotted in relation to an axis sensor voltage 20 and in relation to an axis lambda 21. A first voltage-lambda characteristic curve 10.1 is shifted by a negative voltage offset 17 and a second voltage-lambda characteristic curve 10.3 is shifted by a positive voltage offset 17 in relation to reference voltage-lambda characteristic curve 10.2. The illustrated lambda range is divided by a marking 12 at lambda=1 into a rich lambda range 11 having lambda<1 and a lean lambda range 13 having lambda>1. Proceeding from a first voltage value 22 of the two-point lambda sensor, in rich lambda range 11, a first slope triangle 14.1 is applied to first voltage-lambda characteristic curve 10.1, a second slope triangle 14.2 is applied to reference voltage-lambda characteristic curve 10.2, and a third slope triangle 14.3 is applied to second voltage-lambda characteristic curve 10.3. Proceeding from a second voltage value 23 of the two-point lambda sensor, in lean lambda range 13, a fourth slope triangle 14.4 is applied to first voltage-lambda characteristic curve 10.1, a fifth slope triangle 14.5 is applied to reference voltage-lambda characteristic curve 10.2, and a sixth slope triangle 14.6 is applied to second voltage-lambda characteristic curve 10.3.

Reference voltage-lambda characteristic curve 10.2 corresponds to the curve of the output signal of an intact, unaged two-point lambda sensor in the exhaust duct of an internal combustion engine in the event of a change in the exhaust gas composition. It has its maximum slope at lambda=1. The jump from a high output voltage to a low output voltage takes place in a comparatively small lambda window. For example, due to aging of the two-point lambda sensor, its output voltage may be shifted by a voltage offset 16, 17. In the present exemplary embodiment, voltage offset 16, 17 is equal over the entire lambda range, i.e., both in rich lambda range 11 and in lean lambda range 13. First voltage-lambda characteristic curve 10.1 results in the case of a negative voltage offset 17, second voltage-lambda characteristic curve 10.3 results in the case of a positive voltage offset 16.

Slope triangles 14.1, 14.2, 14.3, 14.4, 14.5, 14.6 each show a voltage change $\Delta U$, which results in the event of a lambda change $\Delta\lambda$ of equal size for all slope triangles 14.1, 14.2, 14.3, 14.4, 14.5, 14.6, proceeding from particular voltage value 22, 23 of the sensor voltage. Therefore, they represent the slopes of particular voltage-lambda characteristic curve 10.1, 10.3 or of reference voltage-lambda characteristic curve 10.2 at particular voltage values 22, 23. The method according to the present invention utilizes the fact that in the case of reference voltage-lambda characteristic curve 10.2, an unambiguous relationship not only exists between output voltage U of the two-point lambda sensor and lambda $\lambda$, but rather also between output voltage U and the slope of characteristic curve $\Delta U/\Delta\lambda$. If a voltage offset 16, 17 exists, the association between the output voltage and the slope of the characteristic curve no longer applies.

In the case of a positive voltage offset 16, in the event of a predefined lambda change $\Delta\lambda$ and a specific voltage value 22, 23 of the sensor voltage, a lower voltage change $\Delta U$ results in lean lambda range 13 and a higher voltage change results in rich lambda range 11 than in the case of reference voltage-lambda characteristic curve 10.2.

In the case of a negative voltage offset 17, in the event of a predefined lambda change Δλ and a specific voltage value 22, 23 of the sensor voltage, a higher voltage change ΔU results in lean lambda range 13 and a lower voltage change results in rich lambda range 11 than in the case of reference voltage-lambda characteristic curve 10.2.

From the deviation of measured voltage change $\Delta U_{mess}$ from voltage change $\Delta U_{Ref}$ expected for reference voltage-lambda characteristic curve 10.2, a measure of the required compensation of voltage offset 16, 17 is ascertained and a corrected voltage-lambda characteristic curve is calculated, which is congruent with reference voltage-lambda characteristic curve 10.2 in the event of complete compensation. It is therefore also possible to obtain an unambiguous relationship between the sensor voltage and lambda in the case of an aged two-point lambda sensor. Therefore, a continuous lambda regulation upstream from the catalytic converter may also be carried out in a restricted lambda range using a two-point lambda sensor, which is cost-effective in comparison to a broadband lambda sensor.

Figure 2:
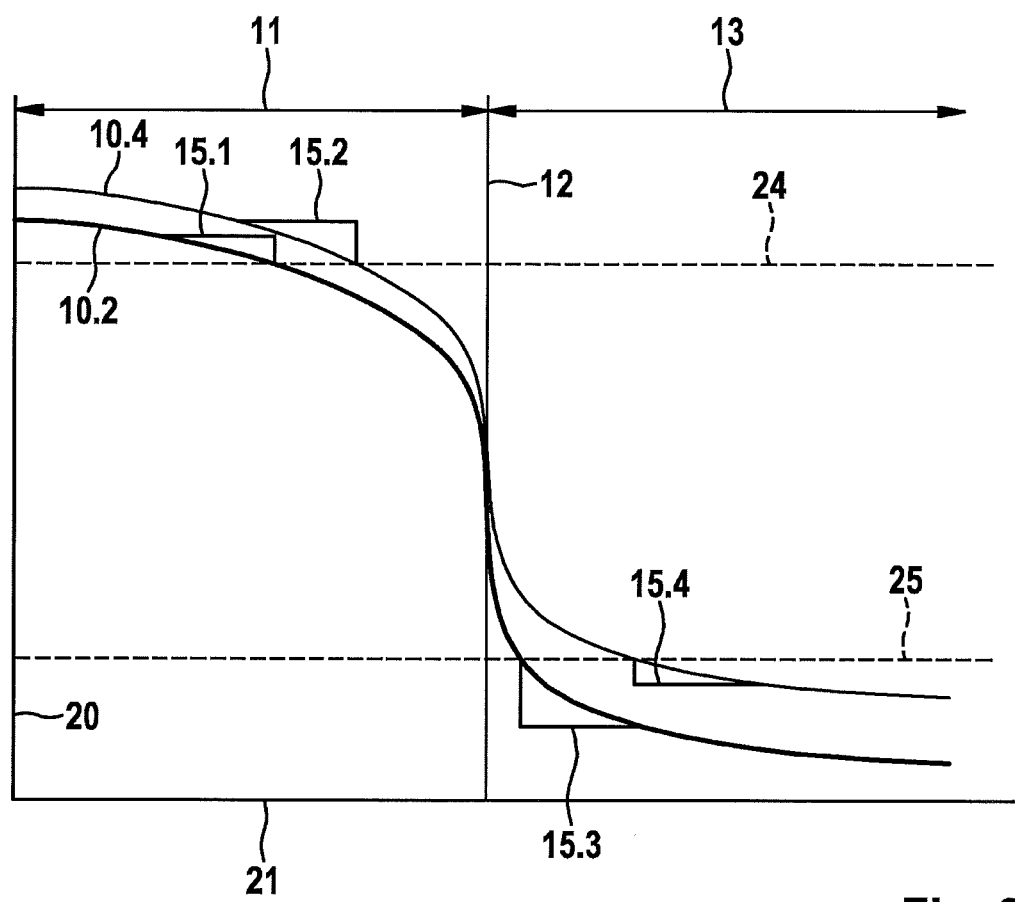
FIG. 2 shows a third voltage-lambda characteristic curve of a two-point lambda sensor having a voltage offset as a function of lambda in relation to a reference voltage-lambda characteristic curve.

FIG. 2 shows a third voltage-lambda characteristic curve 10.4 of a two-point lambda sensor having a voltage offset dependent on the lambda in relation to reference voltage-lambda characteristic curve 10.3 shown in FIG. 1. In the diagram, the same reference numerals as introduced in FIG. 1 are used. At a third voltage value 24 of the two-point lambda sensor, a seventh slope triangle 15.1 is associated with reference voltage-lambda characteristic curve 10.2 and an eighth slope triangle 15.2 is associated with third voltage-lambda characteristic curve 10.4. At a fourth voltage value 25 of the two-point lambda sensor, a ninth slope triangle 15.3 is associated with reference voltage-lambda characteristic curve 10.2 and a tenth slope triangle 15.4 is associated with third voltage-lambda characteristic curve 10.4.

As shown in FIG. 1, slope triangles 15.1, 15.2, 15.3, 15.4 describe a voltage change in third voltage-lambda characteristic curve 10.4 or reference voltage-lambda characteristic curve 10.2 in the event of a predefined lambda change Δλ and therefore the slope of particular characteristic curves 10.2, 10.4.

In the exemplary embodiment shown, third voltage-lambda characteristic curve 10.4 is shifted in the entire lambda range by a fixed absolute value toward higher voltages. This first effect may occur, for example, in the case of two-point lambda sensors having a pumped oxygen reference due to manufacturing tolerances.

Third voltage-lambda characteristic curve 10.4 is additionally shifted in rich lambda range 11 by a fixed absolute value toward lower voltages. This second effect may occur if the two-point lambda sensor is operated excessively hot.

The first effect is more strongly pronounced than the second effect in rich lambda range 11, so that in total third voltage-lambda characteristic curve 10.4 is also shifted toward higher voltages in rich lambda range 11, however, less than in lean lambda range 13.

In a first method step, the output voltage of the two-point lambda sensor is regulated to fourth voltage value 25. With a predefined lambda change Δλ which now takes place, a voltage change $\Delta U_{mess}$ of the output voltage is determined in accordance with tenth slope triangle 15.4, which is less than voltage change $\Delta U_{Ref}$ expected on the basis of reference voltage-lambda characteristic curve 10.2. A compensation of the voltage offset required for the entire lambda range is carried out from this deviation and fourth voltage-lambda characteristic curve 10.4 is corrected accordingly.

In a second method step, the output voltage of the two-point lambda sensor is regulated to third voltage value 24. With a predefined lambda change Δλ which now takes place, a voltage change $\Delta U_{mess}$ of the output voltage results in accordance with eighth slope triangle 15.2, which is greater than voltage change $\Delta U_{Ref}$ expected on the basis of reference voltage-lambda characteristic curve 10.2. The remaining compensation of the voltage offset required for rich lambda range 11 is carried out from this deviation for rich lambda range 11. The voltage-lambda characteristic curve thus obtained is now adapted in the entire lambda range to reference voltage-lambda characteristic curve 10.2.

Alternatively to the compensation of the voltage offset, the cause of a voltage offset may also be recognized from the curve of the voltage offset as a function of lambda, and may thereupon be ended or at least reduced. In the exemplary embodiment shown in FIG. 2, for example, the power of an electrical heater of the two-point lambda sensor may be reduced to decrease the second effect.

An unambiguous determination of an existing voltage offset may be carried out from the comparison of the slope of voltage-lambda characteristic curve 10.1, 10.3, 10.4 to the slope of a reference voltage-lambda characteristic curve 10.2 at voltage values 22, 23, 24, 25, which are to be predefined in each case, of the output voltage of the two-point lambda sensor and therefore in predefined lambda ranges. The voltage offset may be ascertained separately for various lambda ranges and corrected accordingly. The ascertained offset compensation may be checked for plausibility by repeating the measurement at the same point or at other points of voltage-lambda characteristic curve 10.1, 10.3, 10.4. The compensation may be improved by averaging or filtering the measuring results.

In systems which permit an overrun adjustment, the ascertained compensation of the voltage offset may also be checked for plausibility by an overrun adjustment.

In the case of a use in a motor vehicle, it is advantageous to store the offset compensation which was ascertained in a preceding driving cycle and apply it in the next driving cycle. A corrected characteristic curve is therefore immediately available in the next driving cycle. The offset compensation ascertained in the preceding driving cycle may be used for the plausibility check of offset measurements in the running driving cycle.

Voltage values 22, 23, 24, 25 may be actively set. This is advantageous if an offset compensation from an earlier driving cycle is not yet present. If an offset compensation is already present, the adjustment may be carried out passively, if a required voltage value 22, 23, 24, 25 is present during the regular operation of the internal combustion engine.

What is claimed is:

1. A method for compensating for a voltage offset in a voltage-lambda characteristic curve of a two-point lambda sensor in relation to a reference voltage-lambda characteristic curve of the two-point lambda sensor, the two-point lambda sensor being situated in an exhaust duct of an internal combustion engine, the method comprising:
   for an output voltage of the two-point lambda sensor, determining one of a slope and a measure of the slope of the voltage-lambda characteristic curve;
   comparing the determined one of the slope and the measure of the slope to one of a slope and a measure of the slope of the reference voltage-lambda characteristic curve at an equal output voltage; and
   determining the voltage offset from a deviation of the determined one of the slope and the measure of the slope of the voltage-lambda characteristic curve from the one of the slope and the measure of the slope of the reference voltage-lambda characteristic curve.

2. The method as recited in claim 1, wherein proceeding from the output voltage of the two-point lambda sensor, the comparing step comprises comparing a measured voltage change of the two-point lambda sensor after a predefinable lambda change to a reference voltage change of the reference voltage-lambda characteristic curve in the event of an equal lambda change, wherein the voltage offset is determined from a deviation of the measured voltage change from the reference voltage change.

3. The method as recited in claim 2, wherein at least one of:
the predefinable lambda change is set intentionally, and
the determination of the voltage offset is carried out in the event of a system-related lambda change.

4. The method as recited in claim 2, wherein at least one of:
the determining step comprises determining the measured voltage change, repeatedly proceeding from the output voltage of the two-point lambda sensor; and
the determining step comprises determining the measured voltage change in the case that the predefinable lambda change includes positive and negative predefinable lambda changes, wherein the determination of the voltage offset is carried out from one of an averaged and filtered measured voltage change.

5. The method as recited in claim 2, further comprising:
determining additional measured voltage changes in addition to the measured voltage change, proceeding from different output voltages of the two-point lambda sensor, wherein the voltage offsets determined therefrom are checked for plausibility by comparison.

6. The method as recited in claim 2, wherein at least one of an absolute value, a type, and a duration of the predefinable lambda change is selected as a function of one of an exhaust gas condition and an operating condition of the internal combustion engine.

7. The method as recited in claim 1, wherein one of:
the voltage offset is determined for an entire lambda range of the two-point lambda sensor, and
values of the voltage offset are determined for a plurality of lambda ranges.

8. The method as recited in claim 7, wherein the plurality of lambda ranges includes a rich lambda range and a lean lambda range.

9. The method as recited in claim 1, further comprising:
comparing the determined voltage offset of the measured output voltage of the two-point lambda sensor to the reference voltage-lambda characteristic curve, and checking for plausibility of the determined voltage offset by an adjustment of the measured output voltage in the event of an overrun fuel cutoff of the internal combustion engine.

10. The method as recited in claim 1, wherein at least one of:
the determined voltage offset of the voltage-lambda characteristic curve is completely or partially compensated for, and
the determined voltage offset is compensated for as a function of a lambda range of the voltage-lambda characteristic curve.

11. The method as recited in claim 1, wherein at least one of:
causes of the voltage offset are determined, and
measures for avoiding or reducing the causes of the voltage offset are determined based on a curve of the voltage offset as a function of lambda.

12. The method as recited in claim 1, wherein one of:
an output voltage of the two-point lambda sensor is predefined for determining the voltage offset, and
the voltage offset is determined when the output voltage is predefined based on a desired operating condition of the internal combustion engine.

13. A control unit for controlling an internal combustion engine and for determining an output voltage of a two-point lambda sensor in an exhaust duct of the internal combustion engine, comprising:
an arrangement for setting a predefinable lambda change of the exhaust gas;
an arrangement for determining a voltage change of the two-point lambda sensor as a reaction to the defined lambda change;
an arrangement for storing a reference voltage-lambda characteristic curve of the two-point lambda sensor;
an arrangement for comparing the determined voltage change of the two-point lambda sensor after the predefinable lambda change to a reference voltage change of the reference voltage-lambda characteristic curve in the event of an equal lambda change;
an arrangement for determining a voltage offset of a present voltage-lambda characteristic curve of the two-point lambda sensor in relation to the reference voltage-lambda characteristic curve from a deviation of the determined voltage change from the reference voltage change.

* * * * *